US007213473B2

(12) United States Patent
Mosier et al.

(10) Patent No.: US 7,213,473 B2
(45) Date of Patent: May 8, 2007

(54) SAMPLE PREPARATION SYSTEM FOR MICROFLUIDIC APPLICATIONS

(75) Inventors: Bruce P. Mosier, San Francisco, CA (US); Robert W. Crocker, Fremont, CA (US); Kamlesh D. Patel, Dublin, CA (US); Cindy K. Harnett, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 300 days.

(21) Appl. No.: 11/016,310

(22) Filed: Dec. 15, 2004

(65) Prior Publication Data

US 2006/0127238 A1    Jun. 15, 2006

(51) Int. Cl.
*G01F 1/37*        (2006.01)

(52) U.S. Cl. .................................... 73/861.52

(58) Field of Classification Search ................. 137/827, 137/806, 807; 204/450, 600; 73/861.52, 73/861.58
See application file for complete search history.

(56) References Cited

U.S. PATENT DOCUMENTS

| 4,656,448 A | * | 4/1987 | Luetzow ...................... 335/262 |
| 6,224,728 B1 | * | 5/2001 | Oborny et al. .............. 204/450 |
| 6,725,731 B2 | * | 4/2004 | Wiklund et al. ......... 73/861.52 |

* cited by examiner

*Primary Examiner*—Jewel Thompson
(74) *Attorney, Agent, or Firm*—Donald A. Nissen

(57) ABSTRACT

An apparatus that couples automated injection with flow feedback to provide nanoliter accuracy in controlling microliter volumes. The apparatus comprises generally a source of hydraulic fluid pressure, a fluid isolator joined to the outlet of the hydraulic pressure source and a flow sensor to provide pressure-driven analyte metering. For operation generally and particularly in microfluidic systems the hydraulic pressure source is typically an electrokinetic (EK) pump that incorporates gasless electrodes. The apparatus is capable of metering sub-microliter volumes at flowrates of 1–100 µL/min into microsystem load pressures of up to 1000–50 psi, respectively. Flowrates can be specified within 0.5 µL/min and volumes as small as 80 nL can be metered.

20 Claims, 4 Drawing Sheets

SAMPLE PREPARATION SYSTEM FOR MICROFLUIDIC APPLICATIONS

STATEMENT OF GOVERNMENT INTEREST

This invention was made with Government support under contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

CROSS-REFERENCE TO RELATED APPLICATIONS

Not Applicable

FIELD OF THE INVENTION

The present invention is directed to an apparatus that combines automated injection with flow feedback for high precision fluid metering and control generally and particularly for fluid flow control and metering in microfluidic systems. The apparatus additionally provides for multiple, independent sample injection.

BACKGROUND OF THE INVENTION

Sample preparation for capillary or chip-based bioassays typically consists of preparing a sample (analyte) for a particular assay by concentrating the sample by some means, such as by centrifuging or decanting and diluting with an appropriate buffer solution. For ease of identification of the components it can be particularly desirable to "tag" the sample with an appropriate tag or tracer that can be a dye that fluoresces when exposed to the appropriate wavelength of light. However, many tag-analyte complexes have a short shelf life and need to be prepared within a day or two of use. For pathogen identification for first responders and for facilities protection it is particularly desirable to have inexpensive, integrated microchemical analysis systems commercially available that are capable of rapid (typically<2 minutes), multiplexed (>20 antigens) analyses. Automated sample preparation with microliter fluid volumes, i.e., a microfluidic analysis system, can increase repeatability and speed of sample preparation and yield more consistent bioassay results. However, bioassay architectures that require the common manipulations employed in these systems, such as solvent changes, sample preparation and concentration, cannot be implemented without active flow control.

SUMMARY OF THE INVENTION

Accordingly, the present invention is directed to an apparatus that couples automated injection with flow feedback for high precision fluid flow control and metering generally and particularly for microfluidic systems. The apparatus comprises generally means for exerting a hydraulic fluid pressure, a fluid isolator fixedly joined to the outlet of the hydraulic fluid pressure means and a flow sensor means joined to the outlet of the fluid isolator to provide pressure-driven analyte metering. For operation generally and particularly in microfluidic systems it is preferred that the high pressure hydraulic pressure means be an electrokinetic (EK) pump. Furthermore, because of the potential for the formation of operation-inhibiting bubbles it is particularly preferred that the EK pump employ gasless electrodes.

It will be appreciated by those of skill in the art that in contrast to the prior art the invention described herein provides for pulseless flow over pressures up to and exceeding 1000 psi and flow rates over two orders of magnitude. Because of the large ratio of pump and flow sensor resistance to microfluidic system resistance, the invention further provides for passive pump isolation, thereby permitting valveless multiplex fluid metering. The apparatus described herein is capable of metering sub-microliter volumes at flowrates of 1–100 µL/min into microsystem load pressures of up to 1000–50 psi, respectively (for constant electric power, pump flowrate and pressure are inversely related). Flowrates can be specified within 0.5 µL/min and volumes as small as 80 nL can be metered.

Advantageously, the present invention provides for the solution to two problems associated with the use of EK pumps for fluid metering. In particular, EK pumps that have a silica-based stationary phase operate most efficiently with a low conductivity electrolyte at pH 8. However, most biological buffers have a conductivity, due to dissolved salts, that is high. The result is reduced efficiency and an increased likelihood of bubble nucleation due to Joule heating. By interposing a fluid isolator between the EK pump and the buffer solution, eliminating the need to run the buffer solution through the EK pump, the aforementioned problem is eliminated.

A second problem arises when multiple EK pumps share a common output with substantial backpressure. The stronger pump will push fluid backwards through the weaker, or de-energized pump(s). The architecture of the instant invention provides various solutions to this problem, namely, the use of a capillary flow restrictor as a part of the flow sensor. By way of example, a 27 µm id capillary will drop 500 psi for every 100 µL/min of water, which results in a backflow of only 10 µL/min for a system load of 50 psi. A second solution to the problem of backpressure-induced flow afforded by the invention is that the plunger seal of the flow isolator does not move until a net pressure of about 10–50 psi is applied (the exact pressure required to move the plunger depends upon the plunger cross-section). Consequently, load pressures of up to 50 psi can be encountered without backflow to a de-energized EK pump. Because the EK pump itself is essentially a long (≈1 cm) frit with 60 nm pores, the pump itself strongly resists backflow. These solutions are analogous to passive current control in a resistor network; the majority of the current (flow) will pass through the lowest resistance. The solutions described above combine to give a fluid impedance that permits a backflow of only about 0.8 µL/min of water for an absolute pressure of 50 psi. For pumps delivering fluid at 20 µL/min, this corresponds to a 4% leak rate.

DETAILED DESCRIPTION OF THE INVENTION

Figure 1:
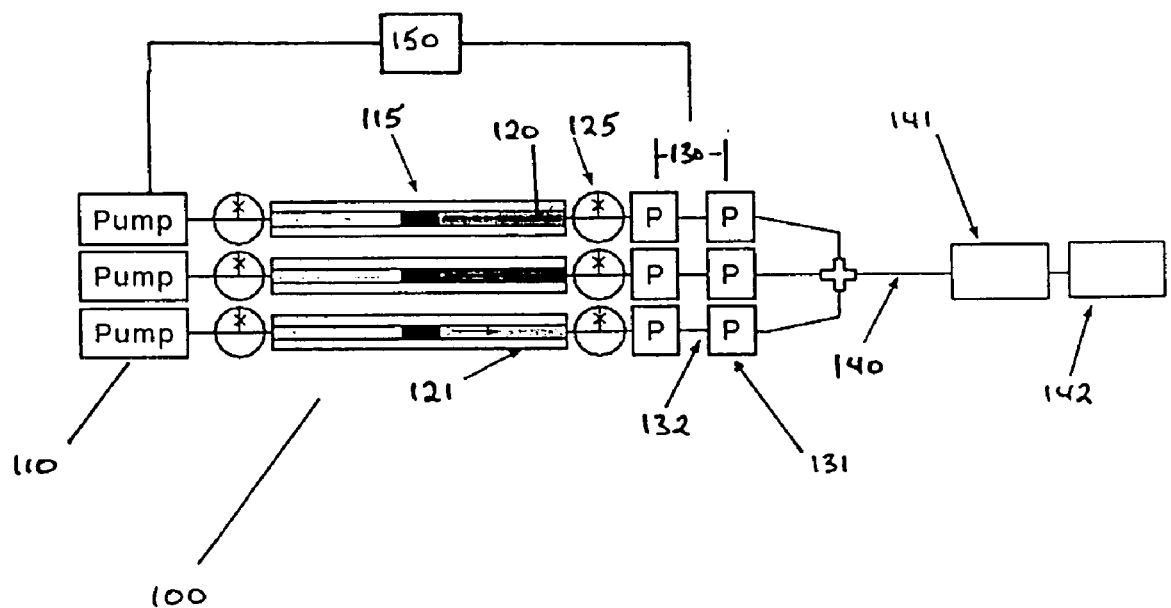
FIG. 1 shows a schematic diagram of the invention.

The present invention, an apparatus for automated fluid injection employing flow feedback for high precision fluid flow control and metering generally and for sample metering and manipulation in particular, is illustrated and exemplified generally by the embodiment shown in FIG. 1. It should noted that while the discussion below is centered around a single sample injection apparatus, a plurality of apparati can be joined in parallel to a common outlet, as further illustrated in FIG. 1, to provide for multiple and independent sample injections into an analysis means.

Referring now to FIG. 1, the high precision fluid metering device 100 is comprised generally of a source of hydraulic pressure 110, that can be an electrokinetic (EK) pump, whose output is fed into fluid isolator 115 and is used to drive the actuator 120 of the fluid isolator. The analyte as well as other solutions can be introduced into the system through checkvalves or tees 125. A reservoir including a plurality of reservoirs separately joined to the system or to each other is contemplated. Pressure from EK pump 110 drives the analyte through flow sensors 130 and into an analysis means, which here comprises a capillary gel electrophoresis apparatus 141 and a photomultiplier tube 142.

Figure 2:
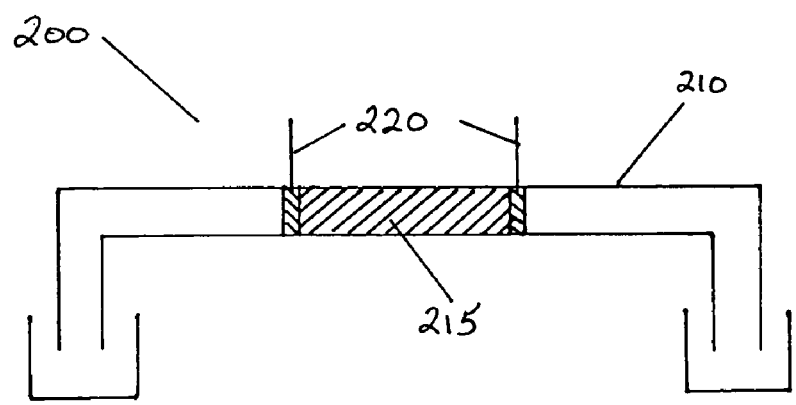
FIG. 2 illustrates a generic electrokinetic pump.

An EK pump comprises an apparatus for converting electric potential to hydraulic force. The hydraulic work produced by an EK pump can therefore, be used to force fluid to flow through a capillary restriction, driving a piston, expanding a bellows or fluid compression generally. A more complete discussion of the theory and operation of EK pumps can be found in U.S. Pat. Nos. 6,013,164 and 6,019,882 to Paul and Rakestraw and in prior co-pending application entitled High Pressure Microhydraulic Actuator, Application No: 10/848,201, filed May 17, 2004. As illustrated in FIG. 2, an electrokinetic pump 200 typically consists of at least one duct or closed channel 210 that can be a closed capillary channel or microchannel that forms an enclosed fluid passageway having an inlet and an outlet. The capillary duct or channel contains an electrolyte and has a porous stationary phase or substrate 215 typically comprising a nonporous dielectric medium disposed therein between one or more pairs of spaced electrodes 220. The porous stationary phase can include small nonporous particles, high surface area structures fabricated within the microchannel, or microporous materials such as monolithic polymer networks. Methods for preparing monolithic polymer networks for use in EK pump applications can be found in U.S. Pat. No. 6,846,399 Castable Three-dimensional Stationary Phase for Electric Field-driven Applicatons, to Shepodd et al., incorporated herein by reference in its entirety.

An electric potential, from a power supply (not shown) is applied between spaced electrodes 220, in contact with electrolyte, or pump fluid, that can be an aqueous or an organic liquid or mixtures thereof, to cause the electrolyte to move in the microchannel by electroosmotic flow and generate a pressure whose magnitude depends on the Darcy permeability of the fluidic channel downstream of the pump. Pump performance in terms of pressure generated per volt of applied electric potential is determined by the composition of the porous dielectric material, the composition of the stationary phase and geometry as well as the properties of the electrolyte. A typical EKP is capable of exerting hydrostatic pressures in excess of 10,000 psi.

For the apparatus disclosed herein, it is particularly desirable to employ an EK pump that exhibits rapid fluid velocity at relatively low voltage (<100 V). It has been found that mm-scale EK pumps, such as described in the application cited above High Pressure Microhydraulic Actuator, possess these desirable characteristics (e.g., pressures up to 1500 psi (10 MPa) and flowrates up to 200 µL/min.

The most common electrode in use in EK pumps generally is a metal wire, principally because of both the ease of insertion into the small dimensions of a microfluidic channel and sealing against high pressure. These wires are generally made of nickel, steel, platinum, gold, or other passive or noble metal. The disadvantage attached to the use of these metal wire electrodes in microscale devices, i.e., devices having fluid flow channels≈1 to 1000 µm in diameter, is the formation of gas bubbles, generally arising from the electrolysis of the solvent, e.g., water or acetonitrile. Because of the small dimensions of flow channels in microfluidic devices, these gas bubbles can partially occlude the current path to the electrodes and reduce the pump output. In the worst case, bubbles block the entire flow channel and thereby open the electrical circuit. In flowing separation or detection systems, electrochemically produced hydrogen or oxygen can react with species of interest and bias or vitiate the analysis. Besides electrolytic gas bubble generation, electroactive species in the fluid being analyzed can be electrochemically reduced or oxidized on the exposed electrodes degrading the analysis and/or upsetting the separation or detection chemistry. It is obviously desirable to eliminate or substantially reduce bubble formation. In open or low-pressure systems and devices, conducting polymer or salt bridge devices have been used to separate electrodes away from sensitive areas in the device. However, in high pressure systems liquid permeation or loss of mechanical integrity precludes these conventional solutions. For the reasons discussed above, it is desirable to include gasless or gas-free electrodes in microfluidic systems generally. Consequently, in the apparatus disclosed herein gas-free or gasless electrodes were used. Methods for making these electrodes can be found in prior co-pending application Ser. No. 10/848,196, filed May 17, 2004 and entitled Gasless and Gas Bubble-free Electrodes, incorporated herein by reference in its entirety.

Briefly, isolation of electrolysis gas from the fluid stream is achieved with Nafion® tubing in two high-current, high-pressure, compact electrodes: a flow-through titanium/Nafion® cathode and a flexible platinum/Nafion® anode. It consists of Nafion® tubing bonded inside a titanium frit with faces that have been sealed with epoxy. A titanium frit with 2-µm porosity is used as a cathode metal because it provides an exit path for electrolysis gases, and the frit provides a rigid mechanical support for squeezing an O-ring or machined face to achieve a high-pressure seal. Titanium is electrochemically inert as a cathode, i.e., it does not passivate or corrode.

Fluid isolator 115 is a microfluidic transducer and is designed to transmit the hydraulic force provided by the EK pump while separating the EK pump fluid from the analyte buffer. The fluid isolator comprises generally a sliding seal or actuator 120, such as the plunger of a hypodermic syringe contained within a liquid-tight cylinder 121. It is preferred that the actuator be inert to both the EK pump fluid and analyte and most preferably be a fluorocarbon material such as Teflon.

Flow rate of the analyte is monitored by flow sensing means 130 such as a calibrated capillary flow restrictor or a conductivity pulsed time of flight device such as that disclosed in U.S. Pat. No. 6,675,660 Composition Pulse Time-of-Flight Mass Flow Sensor, to Mosier, incorporated herein by reference in its entirety. For the purpose of illustrating operation of the invention the flow rate sensors will comprise two pressure transducers 131 disposed on either side of a calibrated capillary 132.

In order to produce the best quality chromatographic results it is desirable to maintain the solvent volumetric flow rate as constant as possible. For a fixed viscosity fluid, a constant flow rate can be maintained by using a controller 150 to control the output of the hydraulic fluid pressure means in order to maintain a constant differential pressure at the outlet of flow sensor means 130. In the example given here the hydraulic fluid pressure means is an EK pump and thus, the controller adjusts the EK pump voltage to maintain the desired constant differential pressure at the outlet of flow sensor means 130.

Operation of a typical sample injection apparatus is illustrated in the examples below. These examples only serve to illustrate the invention and are not intended to be limiting. Modifications and variations may become apparent to those skilled in the art, however these modifications and variations come within the scope of the appended claims. Only the scope and content of the claims limit the invention.

Figure 3:
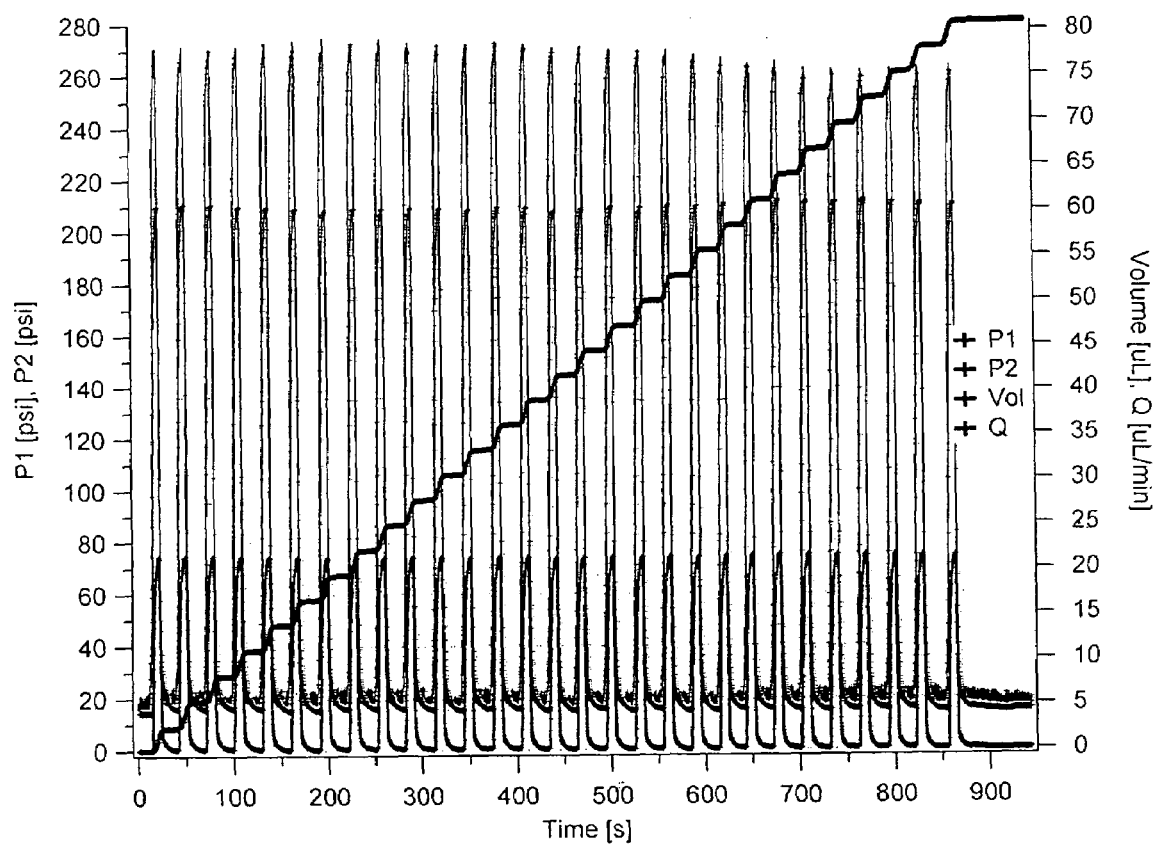
FIG. 3 shows a series of 29 constant voltage injections.
Figure 4:
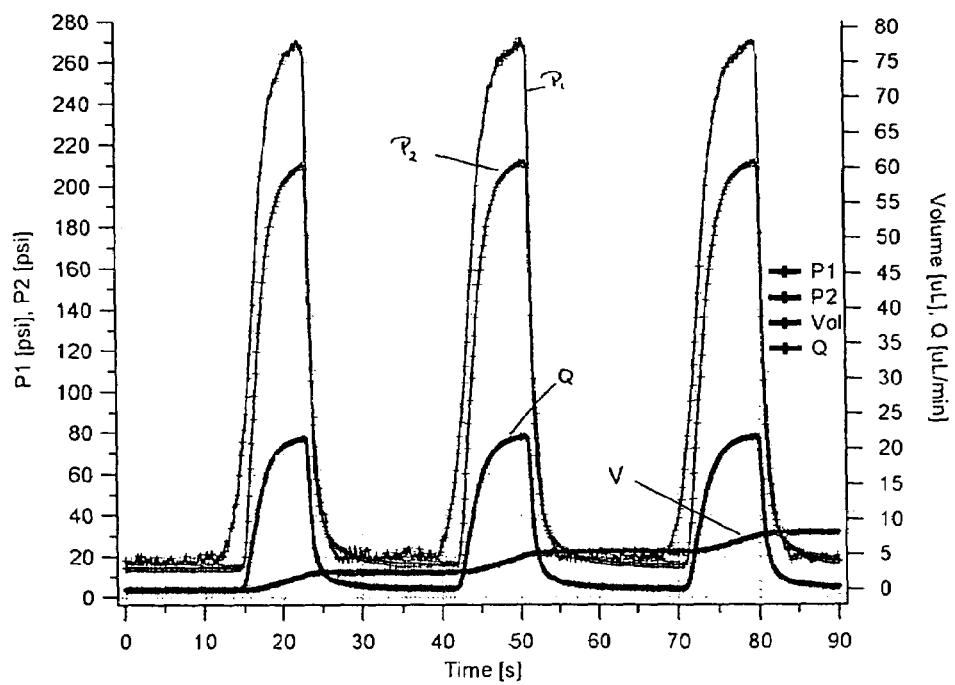
FIG. 4 illustrates details of individual constant voltage injections.

FIG. 3 shows a series of 29 open-loop (i.e., constant voltage) injections of 2.7 μL each from a 100 μL reservoir. The details of individual injections are shown in FIG. 4. The curves shown in FIG. 4 depict the pressures applied to the apparatus ($P_1$ and $P_2$), the volume of fluid injected (V) and the rate of fluid flow (Q). As is obvious from examination of FIGS. 3 and 4, injections in the open-loop mode of operation are repeatable; however, in this mode of operation there is no flow rate or volume control.

When flow feedback is added, closed-loop control becomes possible and the injection flowrate profiles, more desirably, resemble step functions. Moreover, in order to provide rapid and stable flowrate control over a range of flowrates (1–100 μL/min) it is desirable to employ a closed-loop control strategy. Due to compression of any small gas bubbles and system expansion a minimum volume must be metered from the EK pump before steady flow is achieved at the flow sensor. The minimum volume increases with increasing pressure. Also, for a given electric field, the EK pump flowrate decreases with increasing pressure. Because these characteristics yield different times to steady-state for different voltages it is preferred that an algorithm in which gains are functions of flowrate and pressure be used.

Figure 5:
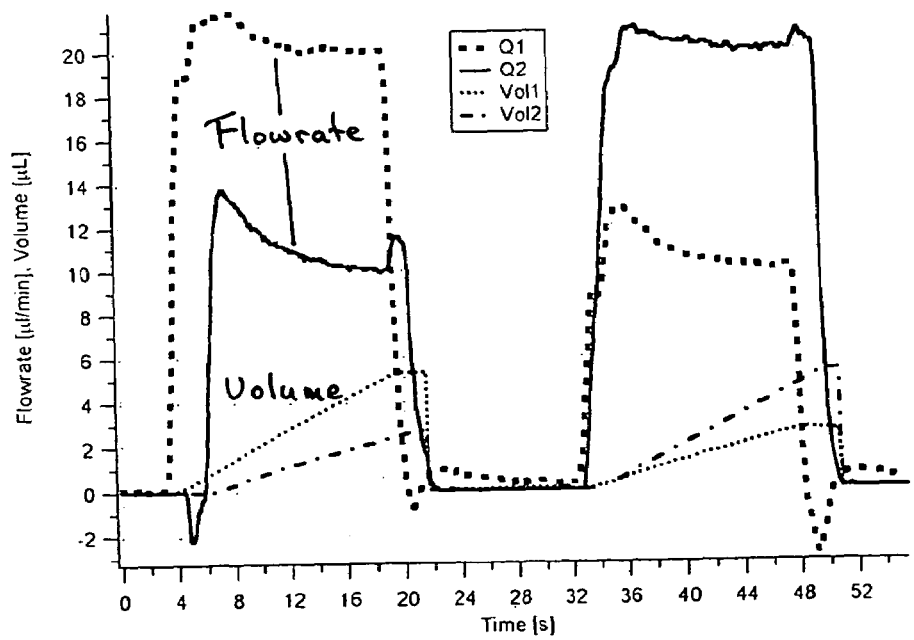
FIG. 5 shows injections employing closed-loop control.

Multiple pumps sharing an input to the sample preparation microfluidics remain largely independent due to their relatively high fluid impedance. Closed-loop control compensates for any remaining influence of one pump on another. FIG. 5 shows simultaneous injections from two EK pumps with a common output and closed-loop control with target volumes corresponding to 2.7 μL and 5.3 μL injected respectively. Different compression volumes (typically the result of small bubbles in the fluid isolators) for each pump result in slightly different times to reach steady state and shut-off. The figure also shows the small, temporary effects from one pump on the other.

Rapid flow control extends the range of volume metering by windowing the lowest flowrates in time to yield small volumes. In the system disclosed herein the slowest flowrate is about 1 μL/min (corresponding to a pressure drop of about 5 psi), although slower flowrates can be obtained with more restrictive flow sensors and/or downstream microfluidics. By way of example, for a target flowrate of 1 μL/min and rise and fall times of 1 second each and a dwell time of 3 seconds, a volume of about 70 nL can be metered. Nanoliter accuracy has been demonstrated on microliter volumes. A series of 160 injections was performed with a single 100 μL reservoir over a period of one week. The average volume metered was 0.52 μL with a standard deviation of 20 nL (4%).

Having demonstrated flow control, a flow rate metering device comprising three pumps, and associated fluid isolators and valving, was connected in parallel (cf. FIG. 1) to perform automated protein labeling and injection to an automated capillary gel electrophoresis (CGE). separation apparatus. Fluorescamine (10 mM) in acetonitrile, protein standards in a borate buffer with some surfactant and water were loaded into the reservoirs. A total volume of 10 μL of fluorescamine and protein were simultaneously injected (at a flowrate of 9:1) into a 0.25 mm capillary 140 joined with the CGE analysis module. After waiting for one minute for the fluorescamine dye to bind to the proteins in the sample, the mixture was metered directly into the CGE apparatus. The resulting CGE separation is shown as curve A in FIG. 6 and compared with a manually labeled protein solution (curve B).

Figure 6:
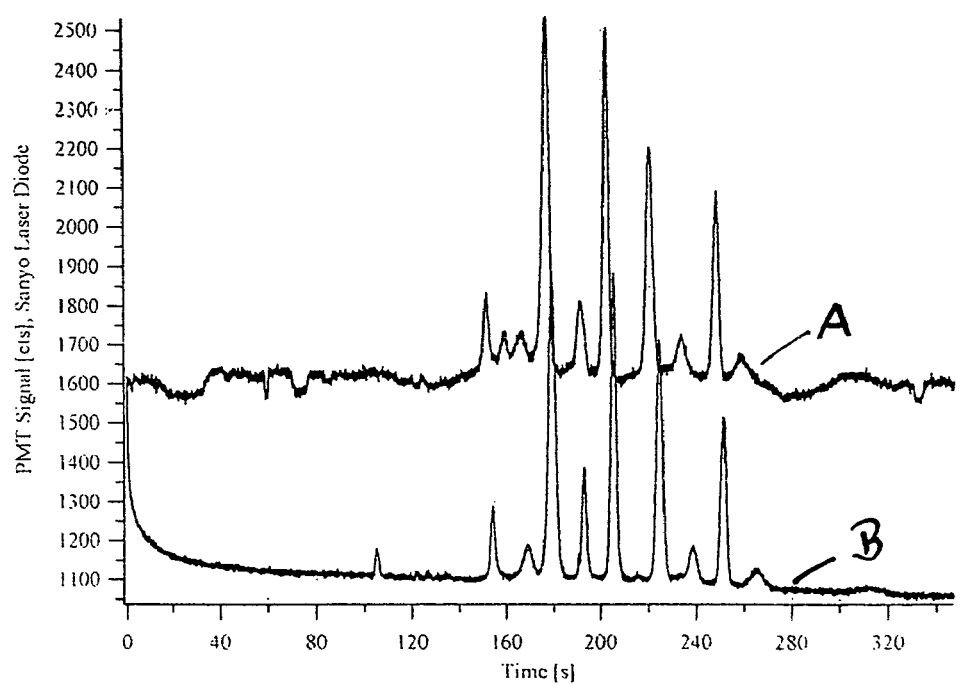
FIG. 6 compares the analysis of labeled protein samples prepared by ted (curve A) and manual (curve B) labeling.

The results shown in FIG. 6 demonstrate clearly that the apparatus described herein provides not only automated sample preparation but also active flow control.

We claim:

1. An apparatus for high precision fluid flow control and metering, comprising, in combination:
   means for exerting hydraulic fluid pressure, having an outlet;
   a microfluidic transducer having an inlet and an outlet, wherein the inlet of said microfluidic transducer is fixedly joined to the outlet of said hydraulic fluid pressure means;
   a flow sensor means joined to the outlet of said fluid isolator; and
   means for providing control of fluid volumetric flow rate in communication with said hydraulic fluid pressure means and said flow sensor means.

2. The apparatus of claim 1, wherein said hydraulic fluid pressure means is an electrokinetic pump.

3. The apparatus of claim 2, wherein the electrokinetic pump includes at least one pair of gasless or gas-free electrodes.

4. The apparatus of claim 3, wherein the electrodes comprise:
   an electronically conducting collector substrate;
   an ionically conducting polymer layer disposed on one or more surfaces of said collector substrate; and
   an electronic conductor making electrical contact with said collector substrate.

5. The apparatus of claim 1, wherein said microfluidic transducer comprises an actuator disposed within a liquid tight cylinder.

6. The apparatus of claim 5, wherein the actuator is a fluorocarbon material.

7. The apparatus of claim 6, wherein the fluorocarbon material is Teflon.

8. The apparatus of claim 1, wherein said flow sensor comprises a capillary flow restrictor disposed between two pressure sensing means.

9. The apparatus of claim 1, wherein control of the fluid volumetric flow rate is by flow feedback.

10. The apparatus of claim 9, wherein flow feedback includes closed loop control.

11. An apparatus for automated labeling of proteins, comprising, in combination:
   means for exerting hydraulic fluid pressure, having an outlet;

a microfluidic transducer having an inlet and an outlet, wherein the inlet of said microfluidic transducer is fixedly joined to the outlet of said high pressure means;

a flow sensor means fixedly joined to the outlet of said fluid isolator, wherein said flow sensor has an inlet and an outlet;

means for providing control of fluid volumetric flow rate in communication with said hydraulic fluid pressure means and said flow sensor means; and a capillary fixedly joined to the outlet of said flow sensor.

12. The apparatus of claim 11, wherein said hydraulic fluid pressure means is an electrokinetic pump.

13. The apparatus of claim 12, wherein the electrokinetic pump includes at least one pair of gasless or gas-free electrodes.

14. The apparatus of claim 11, wherein said flow sensor comprises a capillary flow restrictor disposed between two pressure sensing devices.

15. The apparatus of claim 11, wherein said microfluidic transducer comprises an actuator disposed within a liquid tight cylinder.

16. The apparatus of claim 15, wherein the actuator is a fluorocarbon material.

17. The apparatus of claim 16, wherein the fluorocarbon material is Teflon.

18. The apparatus of claim 11, wherein control of the fluid volumetric flow rate is by flow feedback.

19. The apparatus of claim 18, wherein flow feedback includes closed loop control.

20. A method for automated labeling of proteins, comprising:

providing the apparatus of claim 11;

simultaneously injecting a protein solution and a labeling solution into said capillary;

subsequently flowing the labeled protein into an analysis apparatus.

* * * * *